United States Patent [19]

Hsu et al.

[11] Patent Number: 5,207,937
[45] Date of Patent: May 4, 1993

[54] AMINE SALTS OF SULFUR-CONTAINING ALKYLATED PHENOLS OR ALKYLATED NAPHTHOLS AS MULTIFUNCTIONAL ANTIOXIDANT AND ANTIWEAR ADDITIVES

[75] Inventors: Shih-Ying Hsu, Morrisville, Pa.; Arjun K. Goyal, Woodbury, N.J.; Andrew G. Horodysky, Cherry Hill, N.J.; Liwen Wei, Somerville, N.J.

[73] Assignee: Mobil Oil Corp., Fairfax, Va.

[21] Appl. No.: 692,835

[22] Filed: Apr. 29, 1991

[51] Int. Cl.$^5$ ............................................. C10M 135/30
[52] U.S. Cl. ..................................... 252/33.6; 252/34; 564/281; 564/282; 564/286; 564/287
[58] Field of Search ................ 252/33.6, 34; 564/281, 564/282, 286, 287

[56] References Cited

U.S. PATENT DOCUMENTS

| | | | |
|---|---|---|---|
| 3,778,371 | 12/1973 | Malec | 252/34 |
| 3,962,104 | 6/1976 | Swietlik et al. | 252/34 |
| 4,108,858 | 8/1978 | Malec | 252/34 |
| 4,487,698 | 12/1984 | Idel et al. | 564/281 |

OTHER PUBLICATIONS

CA 70 (9): 36713u.

*Primary Examiner*—Ellen McAvoy
*Attorney, Agent, or Firm*—Alexander J. McKillop; Malcolm D. Keen; Howard M. Flournoy

[57] ABSTRACT

Amine salts of sulfur-containing alkylated phenols or alkylated naphthols, have been found to be effective multifunctional antioxidant and antiwear additives for lubricants.

18 Claims, No Drawings

AMINE SALTS OF SULFUR-CONTAINING ALKYLATED PHENOLS OR ALKYLATED NAPHTHOLS AS MULTIFUNCTIONAL ANTIOXIDANT AND ANTIWEAR ADDITIVES

BACKGROUND OF THE INVENTION

1. Field of the Invention

This application is directed to non-metallic salts of sulfur-containing alkylated phenols and alkylated naphthols as antioxidant and antiwear additives for lubricants and fuels and to compositions containing same.

2. Description of Related Art

Calcium phenates, calcium sulfonates and calcium salicylates have been widely used as metallic detergents for automotive and marine diesel engine lubricants. Their prime function is to act as acid scavenger by neutralizing sulfuric acid generated during the combustion process in diesel engines. Calcium sulfates are produced by the neutralization process and may form deposits, as well as ash, in the engine. In order to minimize or eliminate these deposits, a non-metallic substitute has been synthesized through the derivatization of alkylated phenols and naphthols as shown in this patent application. These compounds show natural alkalinity without undesirably high concentrations of metals, as determined by ASTM standard methods, but can also be moderately overbased like their metallic counterparts. Acid scavenging can be maximized while ash formation can be minimized in this way. These compounds are also very effective antioxidant and antiwear additives for lubricants and fuels.

BRIEF SUMMARY OF THE INVENTION

This invention more particularly provides highly effective multifunctional antioxidant and antiwear additives for lubricant and fuel compositions comprising amine salts of sulfur-containing alkylated phenols and alkylated naphthols and fuel and lubricant compositions comprised thereof.

These amines salts of sulfur-containing alkylated phenols and alkylated napthols demonstrate very promising antioxidant, rust-inhibiting and antiwear characteristics in lubricants. To the best of our knowledge, the syntheses and applications of this family of compounds in lubricant compositions have not been disclosed nor used commercially and are, therefore, novel. Similar antioxidant and thermal stabilizing properties are expected with the use of these additives in fuels.

An object of this invention is to provide improved lubricant and fuel compositions having increased multifunctional antioxidant and antiwear characteristics. The products of this invention are also expected to exhibit corrosion inhibiting, thermal stabilizing, combustion improving, antifatigue, antisquawking, antispalling, high- and low-temperature antioxidation, friction reducing, detergency, dispersancy, extreme pressure and cleanliness properties to lubricants or fuels. It is, also, an object of this invention to provide novel multifunctional lubricant and fuel additives and the novel use of the described additives in such compositions.

The organic quaternary ammonium salts derivatized from sulfurized alkylated phenols and naphthols are an entirely new class of compounds which exhibit both good antioxidant and antiwear properties in mineral oils under severe service conditions without increasing the ash level significantly. These properties can enhance the thermal and oxidative stability of automotive and industrial lubricants to extend their service life.

DESCRIPTION OF THE PREFERRED EMBODIMENTS

The preparation of these novel ashless phenates and naphthates is described in FIGS. 1 and 2. Alkylated phenol can be deprotonated with an organic or inorganic base in a protic or aprotic solvent (FIG. 1). In this case, hydroxide and isopropanol were used. The sodium phenate generated in situ can be quenched with an organic cation, in this case a quaternary ammonium salt was used. Sulfurization was conducted by a standard method using elemental sulfur in decane or other solvents such as ethylene glycol at an elevated temperature to afford the ashless phenate shown in FIG. 1. Any suitable sulfurization methods known to the art can be used. Other solvents which are not sulfur-reactive can also be used for sulfurization reaction. Similarly, alkylated naphthols can be derivatized exactly the same way as described for alkylated phenols (FIG. 2).

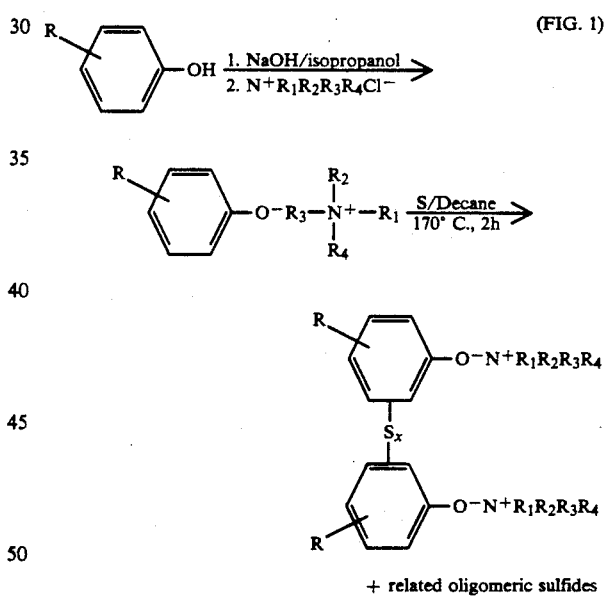

(FIG. 1)

+ related oligomeric sulfides

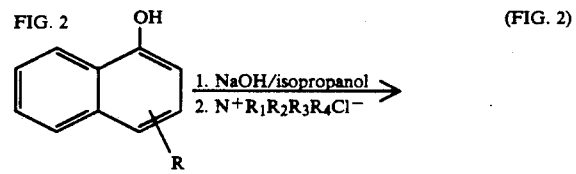

(FIG. 2)

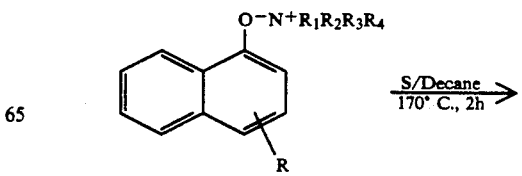

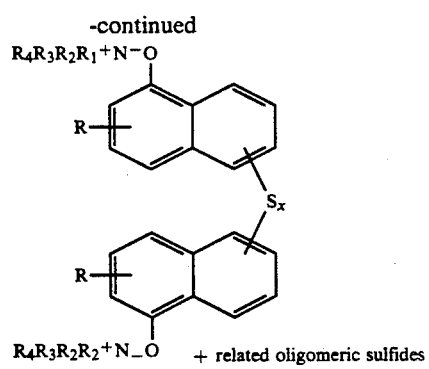

+ related oligomeric sulfides x is indeterminate but the sulfur component is generally a mixture wherein x is 1, 2 or 3, that is, mono-, di-, tri- or polysulfide as is known in the art and as exemplified by the products of Examples 1 and 2 hereinbelow. $R_1$, $R_2$, $R_3$, $R_4$ = hydrocarbyl, preferably $C_1$–$C_{18}$, or aryl, can be the same or different and can optionally contain sulfur, nitrogen and/or oxygen. R = hydrocarbyl, such as alkyl or alkenyl or a polyhydrocarbyl such as polyisobutenyl or mixtures thereof. R, $R_1$, $R_2$, $R_3$ and/or $R_4$ can accordingly be alkyl, alkaryl, aralkyl, etc., or mixtures thereof.

Suitable amine salts include but are not limited to halides such as bromides, chlorides, iodides and the like having the general formula $NR_1R_2R_3R_4X$ where $R_1$, $R_2$, $R_3$, $R_4$ are as defined above or mixtures thereof and optionally containing S, N, and/or O and where X is halide. A highly suitable salt is tricaprylmethylammonium chloride.

Suitable phenols and naphthols may not only be alkylated but may be broadly hydrocarbyl or polyhydrocarbyl-substituted with hydrocarbyl defined as above. Highly suitable reactants are nonylphenol and $C_{12}$ alkylated naphthols.

Both inorganic and organic bases are useful herein. Bases other than sodium hydroxide found to be useful are potassium hydroxide; lithium hydroxide sodium and potassium carbonates or bicarbonates; sodium and potassium hydrides; primary, secondary and tertiary organic amines.

Suitable solvents may be aprotic or protic and include but are not limited to isopropanol, ethylene glycol, toluene, xylenes and ethylene glycol dimethyl ether.

Suitable non-sulfur-reactive solvents include but are not limited to the following: decane solvent, dodecane solvent, or polyalphaolefin solvent and mineral oils.

Conditions for the above reactions may vary widely depending upon specific reactants, the presence or absence of a solvent and the like. Any suitable set of reaction conditions known to the art may be used. Generally stoichiometric quantities of reactants are used. However, more than molar or less than molar or equimolar amounts may be used. The reaction conditions may vary as follows: the reaction temperature may vary from about 30° C. to about 300° C., the pressure may vary from about ambient to slightly higher or autogenous. The time of reaction may vary from about 3 hours to 24 hours or more.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %. It is expected that these materials would also be suitable for use in liquid hydrocarbyl or alcoholic or mixed hydrocarbyl/alcoholic or oxygenated fuel compositions. They are utilized in fuels in amounts of from about 25 to 500 pounds of additive per thousand barrels of fuel and preferably from about 50 to about 250 pounds per 1000 barrels of fuel. Imprvements in cleanliness, corrosion inhibiting, combustion improvement and antiwear properties are expected.

The additives have the ability to improve the above noted characteristics of various oleagenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example from about 45 SSU at 100° F. to about 6000 SSU at 100° F. to about 6000 SSU at 100° F. and preferably, from about 50 to about 250 SSU at 210° F. Oils having viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foam in grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylopropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers. Ester-based lubricants are highly suitable or mixtures thereof.

The fuels contemplated are liquid hydrocarbon combustion fuels, including oxygenated and alcoholic fuels as well as distillate fuels and fuel oils.

It is to be understood, however, that the compositions contemplated herein can also contain other materials. For example, corrosion inhibitors, extreme pressure agents, low temperature properties modifiers and the like can be used as exemplified respectively by metallic phenates, sulfonates, polymeric succinimides, non-metallic or metallic phosphorodithioates, olefin copolymers, esters, axides, and the like. These materials do not detract from the value of the compositions of this invention, rather the materials serve to impart their customary properties to the particular compositions in which they are incorporated.

The following examples are merely illustrative and not meant to be limitations.

EXAMPLE 1

Into a stirred solution of nonylphenol (44 g, 0.2 mol) in isopropanol (100 ml) was added portion-wise to ground sodium hydroxide (8.4 g, 0.21 mol) at 25° C. The mixture was stirred for 30 min and tricaprylylmethylammonium chloride (commercially obtained as Aliquat 336) (81 g., 0.2 mol) was added in portions. Sodium chloride was instantly formed and precipitated. After the addition, the mixture was stirred for 30 min and filtered. The filtrate was evaporated to remove the solvent to afford a yellowish oil into which decane (100 ml) and elemental sulfur (4.4 g) were added. The mixture was heated at 170° C. for 2 hours, cooled to the ambient temperature, and filtered. The solvent was evaporated under reduced pressure to afford the tetra-substituted ammonium salt of sulfurized alkylated phenol as a dark oil (118 g).

EXAMPLE 2

Into a stirred solution of $C_{12}$ alkylated naphthols (obtained by alkylation of a naphthol with $C_{12}$ propylene based olefin tetramer, 31.2 g, 0.1 mol) in isopropanol (100 ml) was added portion-wise to ground sodium hydroxide (4 g, 0.1 mol) at 25° C. The mixture was stirred for 30 min. and tricaprylylmethylammonium chloride (commercially obtained as Aliquat 336) (40.4 g, 0.1 mol) was added in portions. Sodium chloride was formed and precipitated. After the addition, the mixture was stirred for 30 min. and filtered. The filtrate was evaporated to remove the solvent to afford a yellowish oil into which decane (100 ml) and elemental sulfur (3.1 g) were added. The mixture was heated at 170.C for 2 hours, cooled to the ambient temperature, and filtered. The solvent was evaporated under reduced pressure to afford the tetra-substituted ammonium salt of sulfurized alkylated naphthol as a dark oil (66 g).

EVALUATION OF PRODUCTS

The ashless phenates and naphthates obtained as described in the examples were blended into mineral oil and evaluated for antioxidant performance by the Catalytic Oxidation Test at 325° F. for 40 hours (Table 1) and the Four-Ball Wear Test (Table 2). A comparison of the oxidation-inhibiting and antiwear characteristics of the ashless products with their commercial metallic counterpart, 150 TBN calcium phenates (Oronite OLOA 218A), in the same base stocks was also performed.

CATALYTIC OXIDATION TEST

Basically, in the catalytic oxidation test, the lubricant is subjected to a stream of air which is bubbled through at the rate of five liters per hour at elevated temperatures for a specified time (Table 1, 325° F. for 40 hours). Present in the composition are samples of metals commonly used in engine construction, namely, iron, copper, aluminum, and lead.

See U.S. Pat. No. 3,682,980, incorporated herein by reference.

TABLE 1

| | Catalytic Oxidation Test 40 hrs, 325° F. | | |
|---|---|---|---|
| Item | Additive Concentration (wt %) | Change in Acid Number Δ TAN | % Change in Viscosity Δ KV (%) |
| Base oil (200 second, solvent refined, paraffinic neutral mineral oil) | None | 11.97 | 210 |
| Commercial 150 TBN Calcium Phenates (Chevron Oronite OLOA 218A) in above oil | 1.0 | 11.8 | 337 |
| Example 1 in above oil | 1.0 | 12.8 | 156 |
| Example 2 in above oil | 1.0 | 4.1 | 58 |

The data presented above indicates that ashless phenates and naphthates have significantly better antioxidant properties by controlling oxidation-induced acidity and viscosity increases than the commercial calcium phenate. This control of acidity by amine salts is quite remarkable since the inherent basicity of the calcium phenate is so much greater.

FOUR-BALL WEAR TEST

Three stationary balls are placed in the lubricant cup and 1 the lubricant containing the compound to be tested is added thereto, a fourth ball is placed in a chuck mounted on a device which can be used to spin the ball at known speeds and loads. The samples were tested using ½ inch stainless steel balls of 52100 steel for 30 minutes at 200 F under a load of 60 kg at a speed of 2000 rpm.

TABLE 2

| | Four-Ball Wear Test 60 kg/2000 rpm/30 min/200° F. | |
|---|---|---|
| Item | Additive Concentration, wt % | Wear Scar Diameter, mm |
| Base oil (80% solvent paraffinic bright, and 20% solvent paraffinic neutral lubricant oils) | None | 3.32 |
| Commercial 150 TBN Calcium Phenates (Chevron Oronite OLOA 218A) in above oil | 1.0 | 1.92 |
| Example 1 in above oil | 1.0 | 1.69 |
| Example 2 in above oil | 1.0 | 0.93 |

The antiwear data clearly demonstrate that ashless phenates and naphthates possess better antiwear characteristics than th commercial calcium phenate. This property of the novel quaternary amine salts is remarkable given the ashless and non-metallic nature of these phenates and naphthates.

It is clear from the data summarized in Tables 1 and 2 that the organic quaternary ammonium salts derived from sulfurized alkylated phenols and naphthols exhibit much better antioxidant activities than the commercial calcium phenate in lubricants. In addition, the ashless naphthates display much better antiwear properties than the commercial calcium phenate in lubricants. From these data, it can be concluded that the ashless phenates and naphthates described in this patent application are good antioxidants and antiwear additives.

What is claimed is:

1. An improved lubricant composition comprising a major proportion of said lubricant or fuel and a minor multifunctional antiwear, antioxidant proportion of an additive product of reaction comprising an amine salt of a sulfur-containing hydrocarbyl phenol or naphthol prepared from (1) the reaction of a hydrocarbyl phenol or naphthol and a quaternary ammonium salt in the presence of an organic or inorganic base and a protic or aprotic solvent and (2) thereafter reacting in situ the resulting phenol-naphthol quaternary ammonium complex and elemental sulfur in a non-sulfur reactive solvent at temperatures varying from about 25° to about 300° C., pressures varying from ambient to slightly higher or autogenous for a time sufficient to obtain the desired tetra-substituted ammonium salt of sulfurized hydrocarbyl phenol or naphthol.

2. The composition of claim 1 wherein x is a mixture of mono-, di- or polysulfides, the product contains the following generalized structure,

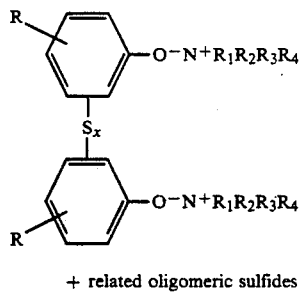

+ related oligomeric sulfides and wherein R is hydrocarbyl or polyhydrocarbyl and $R_1$, $R_2$, $R_3$ and $R_4$ are hydrocarbyl and may be the same or different and optionally contain sulfur, nitrogen and/or oxygen and wherein hydrocarbyl is selected from the group consisting of alkyl, alkenyl, alkaryl, aralkyl or aryl or mixtures thereof.

3. The composition of claim 1 wherein x is a mixture of mono-, di- or polysulfides, the product contains the following generalized structural formula,

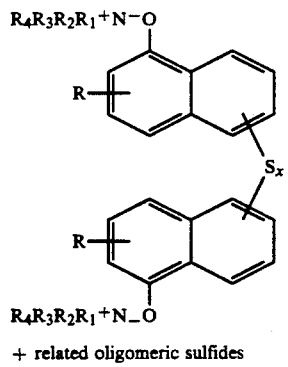

+ related oligomeric sulfides wherein R is hydrocarbyl or polyhydrocarbyl and $R_1$, $R_2$, $R_3$ and $R_4$ are hydrocarbyl and may be the same or different and optionally contain sulfur, nitrogen and/or oxygen and wherein hydrocarbyl is selected from the group consisting of alkyl, alkenyl, alkaryl, aralkyl or aryl or mixtures thereof.

4. The composition of claim 1 wherein the tetra-substituted ammonium salt of sulfurized hydrocarbyl phenol is the product of nonylphenol, tricaprylylmethylammonium chloride and elemental sulfur.

5. The composition of claim 1 wherein the tetra-substituted ammonium salt of sulfurized hydrocarbyl naphthol is derived from $C_{12}$ alkylated naphthols, tricaprylylmethylammonium chloride and elemental sulfur.

6. The composition of claim 1 wherein $R_1$, $R_2$, $R_3$ and $R_4$ are individually selected from $C_1$ to about $C_{18}$ alky or aryl.

7. A lubricant composition in accordance with claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

8. The composition of claim 7 wherein the lubricant is a synthetic oil.

9. A lubricant composition in accordance with claim 1, having therein from about 0.001 to about 10 wt% based on the total weight of the composition of said additive product of reaction.

10. A process of preparing a multifunctional antioxidant, antiwear additive product by (1) the reaction of a hydrocarbyl phenol or naphthol and a quaternary ammonium salt in the presence of an organic or inorganic base and a protic or aprotic solvent and (2) thereafter reacting in situ the resulting phenol-quaternary ammonium complex and elemental sulfur in a non-sulfur reactive solvent in substantially equimolar, less than molar or more than molar ratios at temperatures varying from about 25° C. to about 300° C., pressure varying from ambient to slightly higher or autogenous for a time sufficient to obtain the desired tetra-substituted ammonium salt of sulfurized hydrocarbyl phenol or naphthol.

11. The process of claim 10 wherein x is a mixture of mono-, di- or polysulfides, the product contains the following generalized structure,

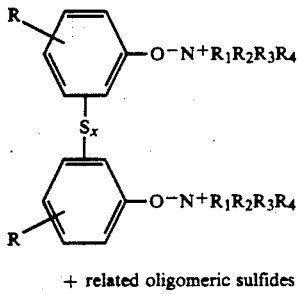

+ related oligomeric sulfides and wherein R is hydrocarbyl or polyhydrocarbyl and $R_1$, $R_2$, $R_3$ and $R_4$ are hydrocarbyl and may be the same or different and optionally contain sulfur, nitrogen and/or oxygen and wherein hydrocarbyl is selected from the group consisting of alkyl, alkenyl, alkaryl, aralkyl or aryl or mixtures thereof.

12. The process of claim 10 wherein x is a mixture of mono-, di- or polysulfides, the product contains the following generalized structural formula,

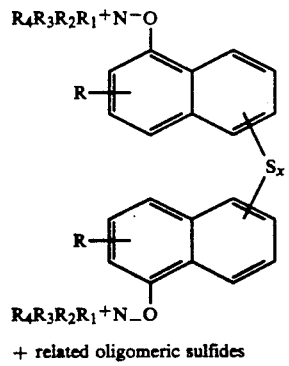

+ related oligomeric sulfides and wherein R is hydrocarbyl or polyhydrocarbyl and $R_1$, $R_2$, $R_3$ and $R_4$ are hydrocarbyl and may be the same or different and optionally contain sulfur, nitrogen and/or oxygen and wherein hydrocarbyl is selected from the group consisting of alkyl, alkenyl, alkaryl, aralkyl or aryl or mixtures thereof.

13. The process of claim 10 wherein the tetra-substituted ammonium salt of sulfurized hydrocarbyl phenol is the product of nonylphenol, tricaprylylmethylammonnium chloride and elemental sulfur.

14. The process of claim 10 wherein the tetra-substituted ammonium salt of sulfurized hydrocarbyl naphthol is derived from C12 alkylated naphthols, tricaprylylmethylammonium chloride and elemental sulfur.

15. The process of claim 10 wherein $R_1$, $R_2$, $R_3$ and $R_4$ are individually selected from $C_1$ to about $C_{18}$ alkyl or aryl.

16. The process of claim 10 wherein the base is selected from the group consisting of sodium hydroxide, potassium hydroxide; lithium hydroxide; sodium and potassium bicarbonates or carbonates and organic amines.

17. The process of claim 10 wherein the solvent is selected from the group consisting of isopropanol ethylene glycol, ethylene glycol dimethyl ether, toluene and xylenes.

18. The process of claim 10 wherein the non-sulfur-reactive solvent is selected from the group consisting of decane solvent, dodecane solvent or polyalphaolefin solvent and mineral oils.

* * * * *

UNITED STATES PATENT AND TRADEMARK OFFICE
CERTIFICATE OF CORRECTION

PATENT NO. : 5,207,937

DATED : May 4, 1993

INVENTOR(S) : Shih-Ying Hsu, Arjun K. Goyal, Andrew G. Horodysky, and Liwen Wei

It is certified that error appears in the above-identified patent and that said Letters Patent is hereby corrected as shown below:

Col. 7, line 20: "of fuel" should be deleted.

Col. 7, line 39: "x is a mixture of mono-, di- or polysulfides" should be deleted.

Col. 7, line 58: -- 1, 2, or 3 -- should be inserted.

Col. 7, line 65: "x is a mixture of mono-, di- or polysulfides" should be deleted.

Col. 8, line 17: -- 1, 2, or 3 -- should be inserted.

Col. 8, line 66: "x is a mixture of mono-, di- or polysulfides" should be deleted.

Col. 9, line 21: "-- 1, 2, or 3 --" needs to be inserted.

Col. 9, line 40: " x is a mixture of mono-, di- or polysulfides" should be deleted.

Col. 10, line 17: -- 1, 2, or 3 -- should be inserted.

UNITED STATES PATENT AND TRADEMARK OFFICE
CERTIFICATE OF CORRECTION

PATENT NO. : 5,207,937
DATED : May 4, 1993
INVENTOR(S) : Shih-Ying Hsu, et. al.

It is certified that error appears in the above-indentified patent and that said Letters Patent is hereby corrected as shown below:

Col. 3, line 16: "tri" should be deleted.

Signed and Sealed this

Twenty-sixth Day of April, 1994

Attest:

BRUCE LEHMAN

*Attesting Officer*  *Commissioner of Patents and Trademarks*